United States Patent
Gagel et al.

(10) Patent No.: US 10,322,219 B2
(45) Date of Patent: Jun. 18, 2019

(54) METHOD OF DETERMINING THE PRESSURE IN AN EXTRACORPOREAL CIRCUIT

(71) Applicant: Fresenius Medical Care Deutschland GmbH, Bad Homburg (DE)

(72) Inventors: Alfred Gagel, Litzendorf (DE); Benedict Glaser, Schweinfurt (DE); Haitham Ibrahim, Dittelbrunn (DE); Pascal Kopperschmidt, Dittelbrunn (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 614 days.

(21) Appl. No.: 14/785,217

(22) PCT Filed: Apr. 14, 2014

(86) PCT No.: PCT/EP2014/000997
§ 371 (c)(1),
(2) Date: Oct. 16, 2015

(87) PCT Pub. No.: WO2014/170007
PCT Pub. Date: Oct. 23, 2014

(65) Prior Publication Data
US 2016/0067397 A1    Mar. 10, 2016

(30) Foreign Application Priority Data

Apr. 16, 2013 (DE) .................. 10 2013 006 562

(51) Int. Cl.
*A61M 1/36* (2006.01)
*A61M 1/14* (2006.01)
(Continued)

(52) U.S. Cl.
CPC ............ *A61M 1/14* (2013.01); *A61M 1/306* (2014.02); *A61M 1/36* (2013.01); *A61M 1/3607* (2014.02);
(Continued)

(58) Field of Classification Search
CPC .... F04B 43/12; A61M 1/3606; A61M 1/3639; A61M 2205/3331; A61M 2205/3351; A61M 2205/3355; A61M 2201/3365
See application file for complete search history.

(56) References Cited

U.S. PATENT DOCUMENTS 5,964,694 A    10/1999  Siess et al.
8,632,487 B2 *  1/2014  Gunther .............. A61M 1/3639
                                                    604/4.01

(Continued)

FOREIGN PATENT DOCUMENTS

DE    102004023971    12/2005
DE    102009027195    12/2010
(Continued)

OTHER PUBLICATIONS

Berdahl et al., "Introduction to Electronics," Oct. 4, 2009, CCRMA: https://ccrma.stanford.edu/wiki/Introduction_to_Electronics retrieved Mar. 27, 2018.*
(Continued)

*Primary Examiner* — Patrick Hamo
(74) *Attorney, Agent, or Firm* — Jacobson Holman, PLLC

(57) ABSTRACT

The present invention relates to a method of determining the pressure or of a parameter correlated with the pressure in an extracorporeal circuit of a blood treatment apparatus, in particular of a dialyzer, wherein at least one blood pump which is driven by at least one motor is located in the blood circuit, wherein the motor current of the named motor and
(Continued)

the blood flow or a parameter correlated therewith is measured for determining the pressure or the parameter correlated therewith and wherein the pressure p or the parameter correlated therewith is calculated from the measured values.

11 Claims, 5 Drawing Sheets

(51) Int. Cl.
*A61M 1/30* (2006.01)
*F04B 43/12* (2006.01)
*G01L 7/00* (2006.01)
*A61M 1/10* (2006.01)

(52) U.S. Cl.
CPC ........... *A61M 1/3639* (2013.01); *F04B 43/12* (2013.01); *G01L 7/00* (2013.01); *A61M 1/1006* (2014.02); *A61M 1/1039* (2014.02); *A61M 1/1086* (2013.01); *A61M 2205/15* (2013.01); *A61M 2205/3306* (2013.01); *A61M 2205/3331* (2013.01); *A61M 2205/3334* (2013.01); *A61M 2205/3344* (2013.01); *A61M 2205/3351* (2013.01); *A61M 2205/3355* (2013.01); *A61M 2205/3365* (2013.01)

(56) References Cited

U.S. PATENT DOCUMENTS

2012/0150089 A1 6/2012 Penka et al.
2013/0072846 A1 3/2013 Heide et al.

FOREIGN PATENT DOCUMENTS

DE 102010011798 9/2011
EP 2609944 7/2013
WO WO 2009/144522 12/2009

OTHER PUBLICATIONS

Pump Power Calculation, Jul. 9, 2012, Neutrium: https://neutrium.net/equipment/pump-power-calculation/ retrieved Mar. 27, 2018.*
Vogelesang, Hans, "Energy consumption in pumps—friction losses," Apr. 2008, World Pumps, feature: energy saving, http://csmres.co.uk/cs.public.upd/article-downloads/Part%202%20-%20Energy%20consumption%20in%20pumps%20-%20friction%20losses_a7545.pdf retrieved Mar. 27, 2018.*

* cited by examiner

METHOD OF DETERMINING THE PRESSURE IN AN EXTRACORPOREAL CIRCUIT

The present invention relates to a method of determining the pressure or of determining a parameter correlated with the pressure in an extracorporeal blood circuit of a blood treatment apparatus, in particular of a dialyzer, wherein at least one blood pump which is driven by at least one electric motor is located in the blood circuit.

The dialysis apparatus known from the prior art typically have an arterial inlet, a venous inlet and a blood pump in the extracorporeal blood circuit by means of which blood pump the blood is conveyed through the extracorporeal blood circuit from the arterial inlet to the venous inlet and through a dialyzer arranged between them.

Figure 5:
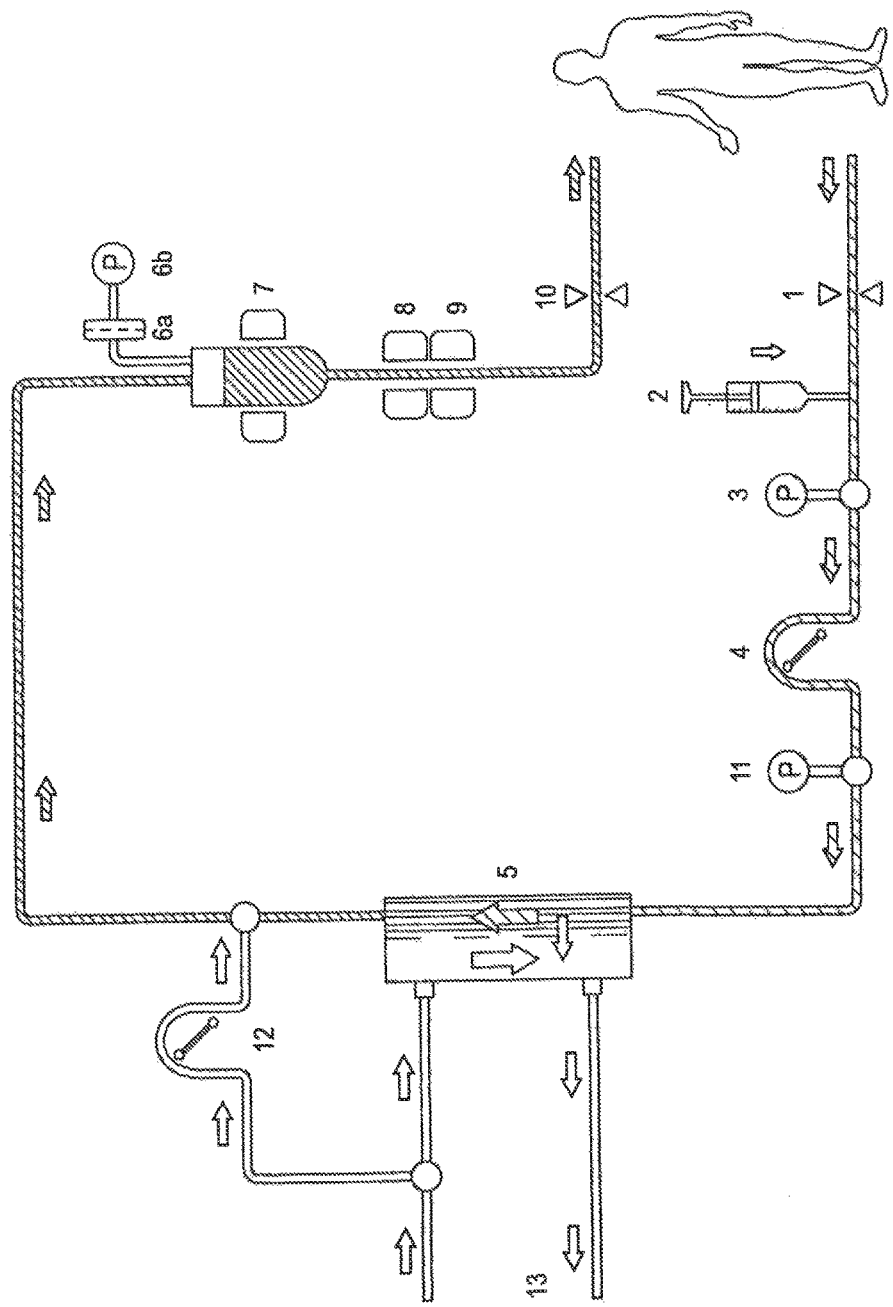

Such a known extracorporeal blood circuit is reproduced in FIG. 5, for example.

The blood moves from the patient out of the arterial inlet through the arterial hose shut-off clamp 1 and via a connector for a heparin pump 2 to the arterial pressure measuring unit 3. The arterial pressure $p_{art}$ is determined in this pressure measuring unit 3. The blood is conveyed by the blood pump 4 which is typically a peristaltic pump which is driven by an electric motor.

The blood moved into a dialyzer 5 after passing through the pump 4, with a pre-filter or post-pump pressure sensor 11 being arranged between the pump 4 and the dialyzer 5 for determining the pressure value $p_{pp}$.

A supply line via which a substitution fluid is conducted into the purified blood by means of a substituate pump 12 is located downstream of the dialyzer 5.

The dialyzer 5 has a blood chamber and a chamber for the dialysis fluid, wherein they are flowed through in counterflow, as is represented by the arrows of the Figure. On the transport of the blood 5 through the blood chamber, blood components such as middle molecules, water, etc. move via the semipermeable membrane of the dialyzer 5 onto the side of the dialysis fluid and are transported away there.

The effectiveness of convective dialysis procedures (H(D)F pre/post/mixed) (HDF=hemodiafiltration; HF=hemofiltration, pre=predilution; post=postdilution; mixed=predilution and postdilution) with high-flux dialyzers is determined in the range of middle molecules such as β2m substantially by the achievable exchange rate $Q_{sub}$ during the treatment. The value $Q_{sub}$ is the substituate flow conveyed by the substituate pump 12. In the embodiment in accordance with FIG. 5, the substituate is added to the blood downstream of the dialyzer 5 so that an HDF postdilution process is present.

A portion of the plasma water flow $Q_p$ is removed from the full blood flow $Q_b$ in the dialyzer 5, which has the consequence that the blood undergoes a certain thickening. In the embodiment shown, this can, for example, mean that the hematocrit $H_{kt}$ at the outlet of the dialyzer increases by 10% to 20% with respect to that at the inlet of the dialyzer.

To dilute the blood back to the original hematocrit, the removed fluid volume is continuously replaced with the substitutate flow $Q_{sub}$ by means of the pump 12 downstream of the dialyzer 5, as shown in FIG. 5. If the substituate flow or the substituate pump 12 has to be stopped, for example due to a conductivity alarm or due to occasional leak tests of the hydraulics, this has the consequence that the blood of higher viscosity thickened in the dialyzer 5 moves via the venous hose system back to the patient.

The reference numeral 13 designates the hydraulics or the balance circuit for the dialyzate flow $Q_d$.

As already stated, the blood moves via a venous needle back to the patient. The venous hose shut-off clamp 10 is located upstream of this venous needle and an optical detector 8 and an air bubble detector 9 are located upstream thereof. Furthermore, a venous bubble trap with a filling level detector 7 is provided between these detectors and the supply line of the substitutate. A hydrophobic filter 6a is connected thereto and is in turn connected to a venous pressure sensor 6b for determining the venous pressure $p_{ven}$.

If the blood of higher viscosity moves back to the patient, the higher viscosity of the blood in the venous needle can in particular result in an additional pressure increase which can amount to 200 mmHg and more under certain circumstances. This can result in an unnecessary shear stress load of the blood. The pressure increase induced by the higher viscosity of the blood can be measured directly at the venous pressure sensor 6b.

It the named pressure increase and the load on the blood associated therewith is to be reduced, there would be the possibility of likewise stopping the blood pump 4 during the standstill time of the substituate pump 12 so that no blood of higher viscosity reaches the patient. In this case, the blood remains in the dialyzer 5. If both pumps 4, 12 start to run again simultaneously, the named hemoconcentration bolus, i.e. the bolus of thickened blood, is not produced. The stopping of the blood pump, however, results in insecurity in the user. There is furthermore a disadvantage in that in the case of a substituate pump and blood pump being stationary for a longer time there is the risk that the blood in the extracorporeal circuit coagulates, which would have the consequence of an unacceptable blood loss.

An alternative possibility for preventing the hemoconcentration bolus would be to reduce the blood flow $Q_b$ and to regulate the blood pump rate in dependence on the venous pressure $p_{ven}$ so that the pressure increase is compensated or attenuated. Such a method is known from WO 2009/144522 A1.

A clotting of blood in the dialyzer and also the named high hemoconcentration of the blood due to a high ultrafiltration can be recognized by means of the pressure sensor 11 shown in FIG. 5 for determining the prefilter pressure or the postpump pressure $p_{pp}$. It is likewise possible by this sensor to detect the presence of a hemoconcentration bolus. A kinking of the blood hose and a pressure increase associated therewith can furthermore be detected by this sensor.

A disadvantage of this sensor comprises, on the one hand, the additional costs caused thereby and, on the other hand, frequently used air-filled pressure lead-off lines. A blood-to-air interface thereby arises at which clotting can take place or at which clotting can start. There is furthermore the risk that blood runs into the interior of the device in the event of a leak, which is subject to corresponding risks with respect to the electrical safety and with regard to cross-contaminations with infectious substances via the device.

It must therefore be endeavored to reliably recognize a kinking of the blood hose, a clotting or also a hemoconcentration increase in the dialyzer with such an additional, invasive pressure sensor.

It is thus the underlying object of the present invention to further develop a method of the initially named kind such that an alternative to the pressure measurement by a pressure sensor is provided.

This object is achieved in accordance with the invention by a method having the features of claim 1. Provision is accordingly made that the motor current $I_M$ of the named motor as well as the blood flow $Q_b$ of at least a parameter correlated therewith is measured for determining the pressure p or the parameter correlated therewith and that the pressure p or the parameter correlated therewith, such as a pressure difference, is calculated from the measured values.

It is thus the underlying idea of the present invention to draw conclusions from the measurement of the motor current $I_M$ or of a parameter correlated therewith and of the blood flow $Q_b$ or of a parameter correlated therewith on the pressure p, preferably conclusions on the pressure p downstream of the blood pump, or to calculate this pressure or also a parameter correlated therewith such as the pressure difference over the pump.

It is thus possible to determine the pressure or also a pressure difference, for example, from the measurement of the named parameter values. The use of an invasive pressure sensor such as is known from the sensor 11 in FIG. 5 in accordance with the prior art can be dispensed with.

It is, for example, conceivable that the pressure difference $\Delta p$ is determined by the method upstream and downstream of the blood pump and between the inlet and outlet of the pump; the pressure $p_{art}$ is determined upstream of the blood pump and/or the pressure $p_{pp}$ is determined downstream of the blood pump.

Provision is made in a further embodiment of the invention that the parameter correlated with the blood flow $Q_b$ is the speed n of the blood pump and/or the angular speed $\omega$ of the blood pump. The parameter correlated with the current can, for example, be the provided electrical power of the power supply of the motor.

The pressure difference upstream and downstream of the blood pump can be determined in accordance with the formula $I_M = a + b \cdot Q_b + c \cdot Q_b \cdot \Delta p$.

Figure 1:
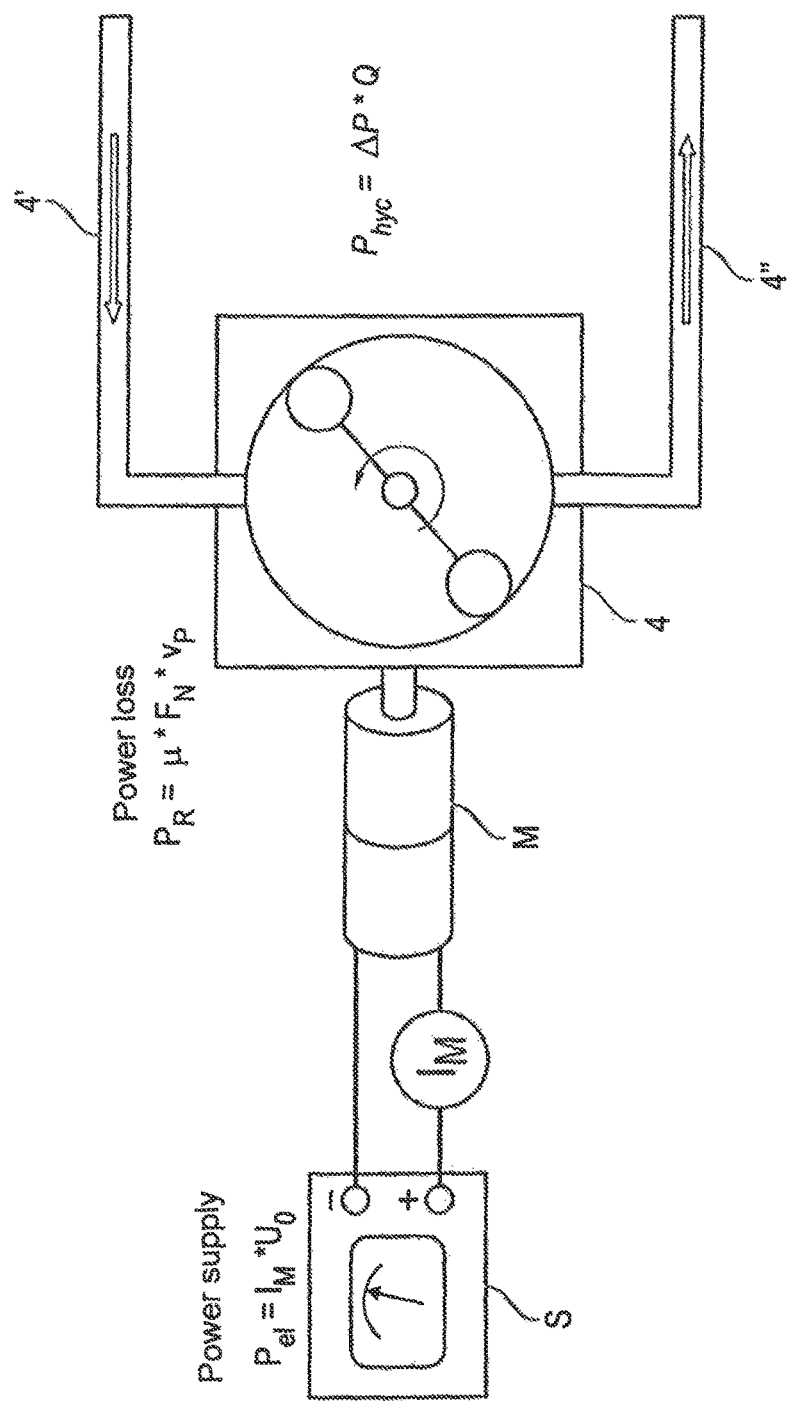

This relationship is produced from the following considerations:

The electric motor with the reference symbol M of a peristaltic pump 4 and its power supply S is shown in FIG. 1. The peristaltic pump is used, for example, at the position of the extracorporeal blood circuit in accordance with FIG. 5 and thus conveys the blood from an inlet 4 to an outlet 4.

The electrical line of the power supply S $P_{el}$ is split into three portions in the drive, namely $P_0$, $P_R$ and $p_{hyc}$. In this respect, $P_{el}$ is the electrical power output by the power supply, i.e. $I_M \cdot U_0$, where $U_0$ is the voltage which is output by the voltage supply, such as 24 V.

The value $P_0$ is the constant power consumption which results, for example, from the control electronics in the BLDC motor, heat losses, iron losses, etc.

The value $P_R = \mu \cdot F_N \cdot v_p$ represents power losses which are proportional to the speed $v_p$ of the pump. They are, for example, friction losses in the bearings of the mechanically moving parts, in the transmission and in the rollers as well as the copper-induced losses in the lines.

The normal force $F_N$ in the pump is produced by the compression of the hose or by the restoring force of the pump hose to achieve the occlusion. This can be generated by tensioned springs.

The power $P_{hcy}$ is the technical power which the pump outputs to the flowing medium, i.e. to the blood. This is determined by $P_{hyc} = Q_b \cdot \Delta p = Q_b \cdot (p_{pp} - p_{art})$.

All the aforesaid pressures are static relative pressures.

The motor current is preferably driven in amperes, the supply voltage $U_0$ in volts, for example $U_0 = 24$ V, $\mu$ as the effective coefficient of friction without a unit, $F_N$ in Newtons, $v_p$ in m/s, $Q_b$ in m³/s and the pressure in Pa.

If the relationships for $P_{el}$, $P_R$ and $P_{hyc}$ are inserted into the relationship $$P_{el} = P_0 + P_R + P_{hyc},$$

the following relationship results:

$$I_M \cdot U_0 = P_0 + \mu \cdot F_N \cdot v_p + Q_b \cdot \Delta p.$$

If this relationship is resolved according to the motor current $I_M$, $$I_M = P_0/U_0 + \mu \cdot F_N \cdot v_p/U_0 + 1/U_0 \cdot Q_b \cdot \Delta p \text{ results.}$$

The speed $v_p$ can be replaced with the speed $n_p$ or by the angular speed $\omega_p$:

$$v_p = 2\pi \cdot R \cdot n_p = R \cdot \omega_p.$$

If the speed $v_p$ is replaced by a further value, namely by the blood flow $Q_b$, $(Q_b = V_S \cdot v_p/(2\pi \cdot R))$, $$I_M = P_0/U_0 + \mu \cdot (F_N/U_0) \cdot (2\pi \cdot R)/V_S \cdot Q_b + 1/U_0 \cdot Q_b \cdot \Delta p$$
finally results.

In this respect, $V_S$ means the stroke volume of the blood pump per revolution [m³], typically 10 mL; R means the radius of the blood pump motor [n]; n the speed of the blood pump [I/s] and co the angular speed [rad/s].

Using the substitutions $a = P_0/U_0$, $b = (\mu \cdot F_N)/U_0 \cdot (2\pi \cdot R)/V_S$ and $c = 1/U_0$, the following equation results:

$$I_M = a + b \cdot Q_b + c \cdot Q_b \cdot \Delta p \quad \text{(Equation (1))}$$

With known parameters a, b and c, this relationship can be resolved according to the pressure difference $\Delta p$. There thus results:

$$\Delta p = I_M/(c \cdot Q_b) - a/(c \cdot Q_b) - b/c = 1/c \cdot (I_M/Q_b - a/Q_b - b).$$

It is possible on measurements of the motor current and of the blood flow through this relationship, with knowledge of the parameters a, b and c, to calculate the pressure difference before and after the pump, i.e. the value $\Delta p$.

The pressure directly after the blood plump, i.e. the value $p_{pp}$, can be calculated from the relationship $\Delta p = p_{pp} - p_{art}$. The arterial pressure $p_{art}$ is measured and $\Delta p$ can be determined from the above-named equation. There thus results:

$$p_{pp} = \Delta p + p_{art}.$$

To increase the accuracy of the fit function, the above-stated equation (1), which reflects the relationship between the motor current, the blood flow and the pressure difference, can be expanded by higher powers, also non-rational powers, of $Q_b$ and $\Delta p$:

$$I_M = \Sigma\Sigma c_{p,b} \cdot Q_b^q \cdot \Delta p^p,$$

where the sums are formed via p=0 to m and q=0 to n, where p, q∈Q

The present invention furthermore relates to a method for regulating or calculating the pressure or a parameter correlated with the pressure in an extracorporeal blood circuit of a blood treatment device, in particular a dialyzer, wherein at least one blood pump which is driven by at least one motor is located in the blood circuit. Provision is made in accordance with this embodiment of the invention that the pressure or a parameter correlated therewith is determined in accordance with a method in accordance with one of the claims 1 to 5 and that the blood flow conveyed by means of the pump is varied for the purpose of regulation or control.

It is thus conceivable to use the above-named determined or calculated pressure values or parameters based thereon, such as the pressure difference over the pump, to set up a regulation process in which the regulation value is the pressure or a parameter correlated therewith such as a pressure difference. The control variable is preferably formed by the blood pump rate, i.e. by the blood flow $Q_b$ or a parameter correlated therewith.

It is conceivable that the method comprises the restriction of the pressure or of a parameter correlated with the pressure such that a limit value may not be exceeded. A pressure regulation is also conceivable and preferred.

It is conceivable that a limit value for a maximum permitted pressure change is predefined, with this pressure change not being measured directly, but rather in accordance with the invention via the observation of the motor current. If this limit value is reached or exceeded, the actual regulation can be started to keep constant the pressure or a parameter correlated therewith.

Provision is made in a preferred embodiment of the invention that the regulation is carried out such that the relationship $(I_M(t)-a)/Q_{b(t)} = (I_{M,0}-a)/Q_{b,0} = \text{const}$ remains constant. The values $I_{M,0}$ and $Q_{b,0}$ are start values of the motor current and of the blood flow at a point in time before the occurrence of a fault, in particular before exceeding the limit value in accordance with claim 7.

The present invention furthermore relates to a blood treatment apparatus having at least one extracorporeal blood circuit in which at least one blood pump is arranged which is driven by at least one electric motor. At least one means is provided for measuring the motor current $I_M$ and at least one means for measuring the blood flow $Q_b$ or of parameters respectively correlated therewith. The blood treatment apparatus comprises at least one calculation unit, control unit or regulation unit which is configured such that it carries out the method in accordance with one of the claims 1 to 10 on the basis of the measured values provided by the means.

The blood pump is preferably a peristaltic pump. Its motor is preferably formed by an electric motor and particularly preferably by a DC motor and, optionally, by a brushless DC motor.

At least one dialyzer, which has at least one chamber flowed through by blood in the operation of the circuit, is located in the extracorporeal circuit. In addition, at least one chamber can be provided which is flowed through by dialysis fluid in operation.

In a further embodiment of the invention, at least one substituate pump is provided which supplies a substitution fluid to the blood in the extracorporeal circuit via a line upstream and/or downstream of the dialyzer.

Provision can finally be made that no pressure sensor is provided downstream of the blood pump, with the exception of a venous pressure sensor, and that preferably no pressure sensor is arranged downstream of the blood pump and upstream of a dialyzer arranged in the extracorporeal blood circuit.

The blood treatment apparatus is preferably designed with means which are suitable to carry out one, more or all the respective method steps in accordance with the method claims.

Figure 2:
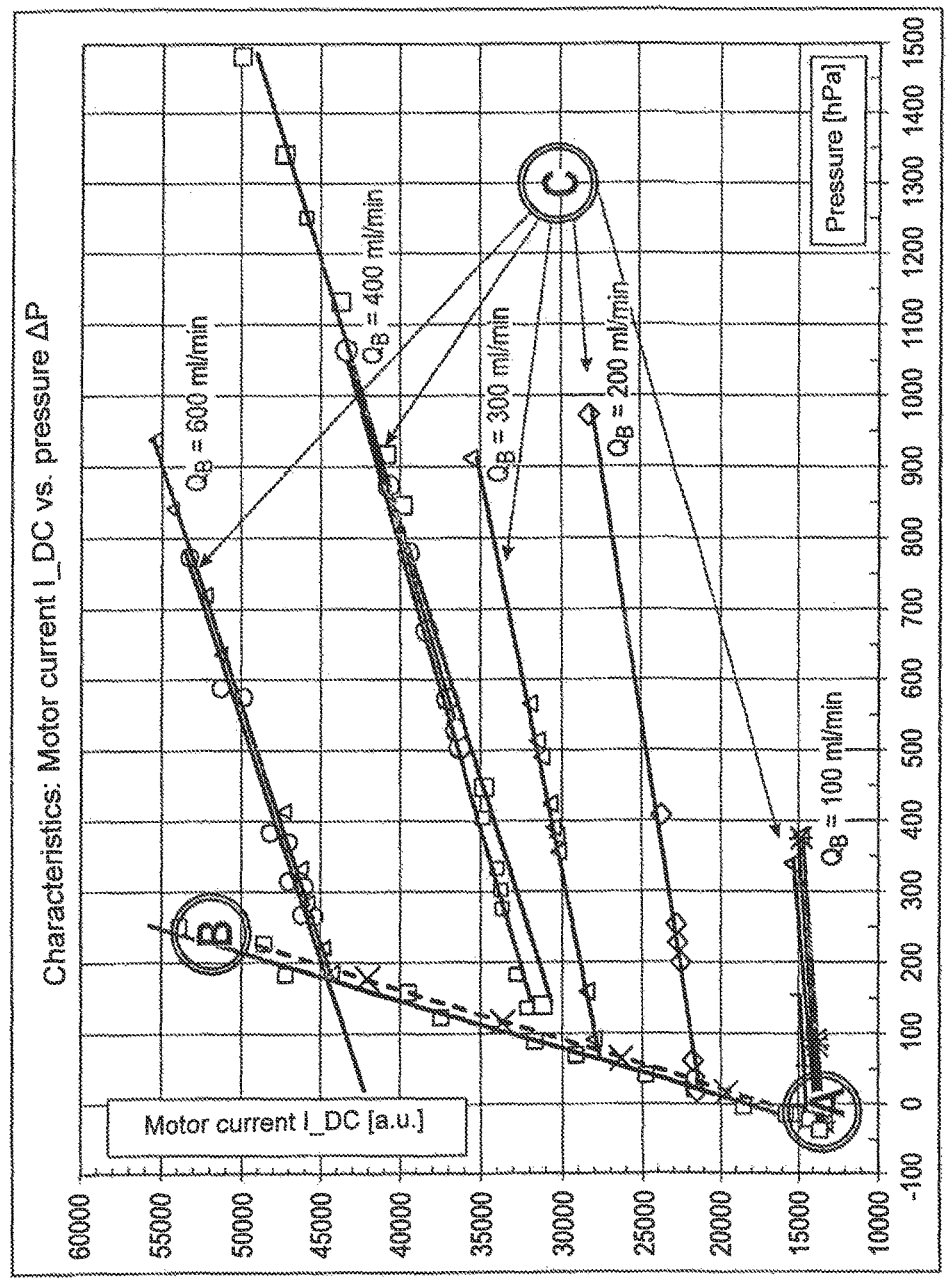
Figure 3:
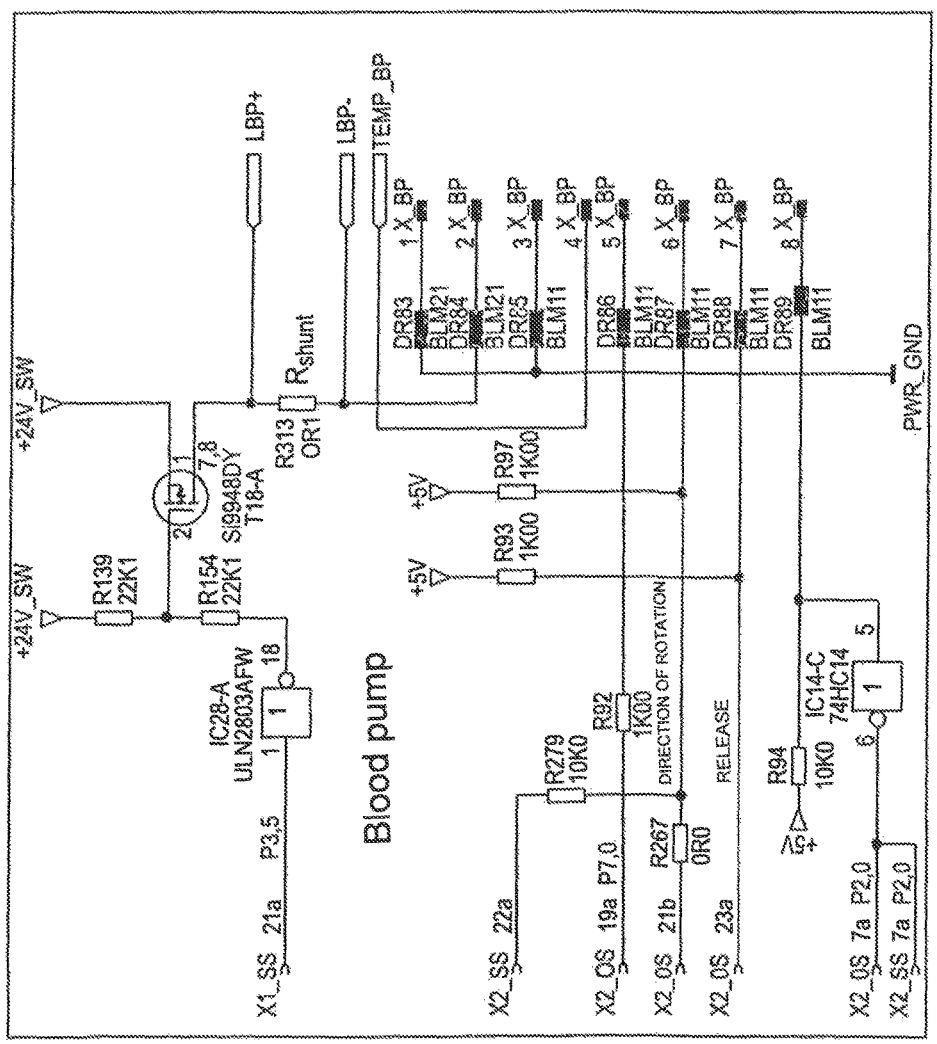
Figure 4:
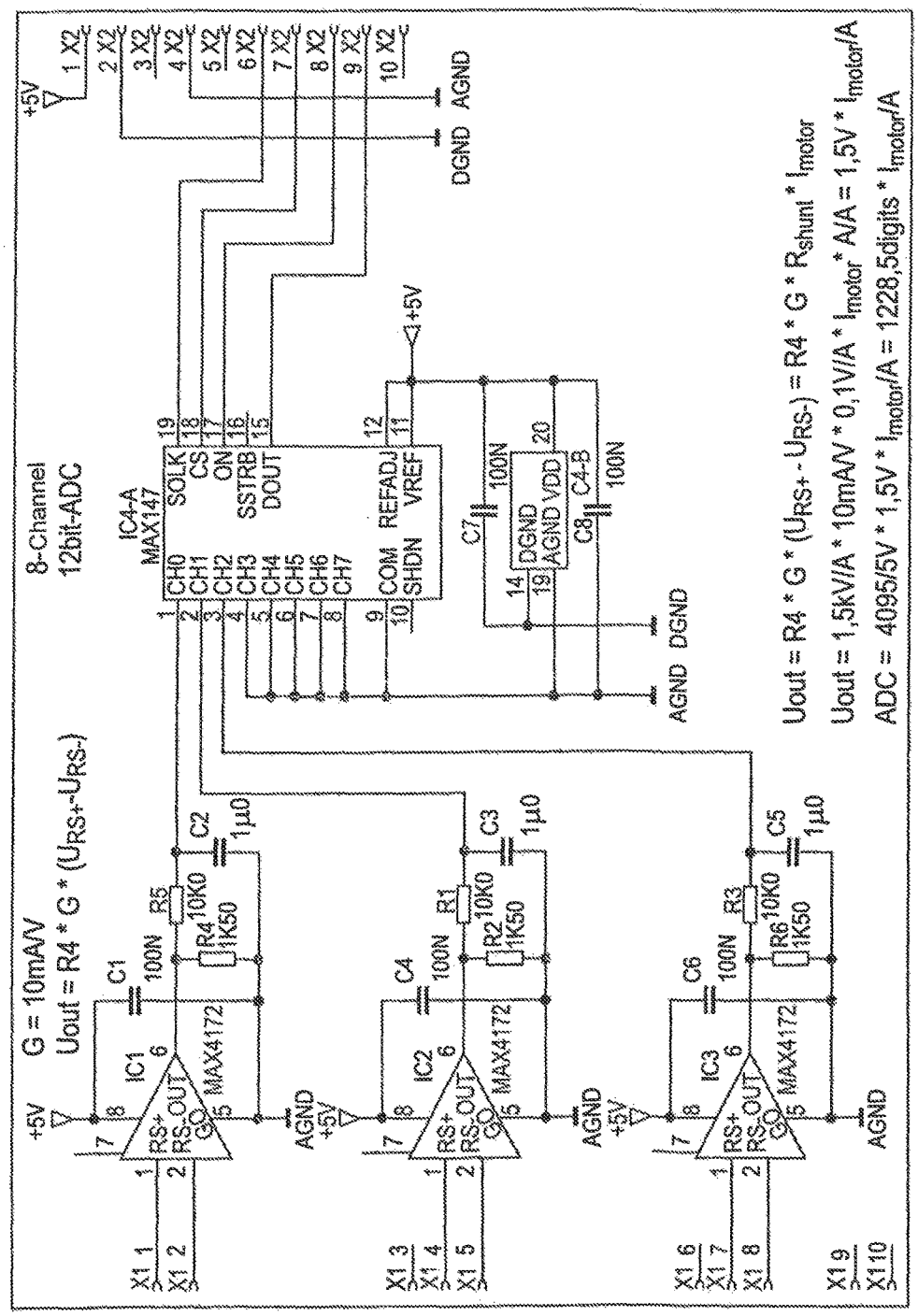

Further details and advantages of the invention will be explained in more detail with reference to an embodiment shown in the drawings There are shown:

FIG. 1; a schematic view of the peristaltic blood pump having a motor and a power supply;

FIG. 2; the dependence of the motor current on the blood flow and the pressure difference over the pump;

FIG. 3: an example for a power supply with a shunt resistance;

FIG. 4 an example for a high-side current measurement with 12-bit ADC; and

FIG. 5: a schematic representation of an extracorporeal circuit of a dialyzer in accordance with the prior art.

As already stated above, in accordance with the invention, a pressure or a parameter correlated therewith, such as the pressure difference before and after the blood pump, can be calculated on the basis of the measurement of the motor current and of the blood flow or of parameters correlated therewith.

This calculated value can be used to carry out a pressure regulation. It can be prevented in this manner that pressure peaks or pressure values arise which may result in damage to the blood.

In a preferred embodiment, the relationship between the motor current, the blood flow and the pressure increase over the pump is reproduced by the following relationship;

$$I_M = a + b \cdot Q_b + c \cdot Q_b \cdot \Delta p.$$

If this equation is resolved for the pressure difference $\Delta p$ it can be seen that the pressure difference can be determined on the basis of the measurement parameters $I_M$ and $Q_b$. In this manner, the pressure downstream of the blood pump can also be calculated on a measurement of the arterial pressure.

Reference is made in this respect to FIG. 5 with regard to the arrangement of the corresponding pressure sensors. FIG. 5 or such an arrangement of an extracorporeal blood circuit is also suitable for the present invention and is covered by it, with provision preferably being made that in accordance with the invention, the pressure sensor 11, i.e. the pressure sensor downstream of the blood pump 4, is dispensed with.

The representation in accordance with FIG. 1 illustrates that the aforesaid relationship of motor current, blood flow and pressure difference over the pump can be determined from the values shown there $P_{el}$, $P_R$ and $P_{hyc}$ or from the relationship $P_{el} = P_0 + P_R + P_{hyc}$.

In FIG. 1, the motor current is likewise given by the reference symbol $I_M$.

FIG. 2 shows the dependence of the motor current as a function of the blood flow and of the pressure or of the pressure difference over the pump based on the above-given relationship $I_M = f(Q_b; \Delta p)$.

As can be seen from FIG. 2, the motor current increases with the pressure difference in accordance with this relationship with a constant blood flow.

The point A in FIG. 2 is characterized by a pressure increase $\Delta p = 0$. No blood flow is present here, either, so that the value a results for the motor current.

The path A-B is characterized by a pressure increase over the pump of approximately 0, with the blood flow varying from 100 to 700 ml/mm. In this case, the change in the motor current $\Delta I_M$ along the path A-B is $\Delta I_M = b \cdot Q_b$.

The paths C shown are each characterized by constant values of the blood flow (100; 200; 300; 400; 500; and 600 ml/mm). The relationship $\Delta I_M = c \cdot Q_b \cdot \Delta p$ hereby results.

If not only a pressure measurement is to be carried out, but also a constant regulation of the pressure, it can be selected which pressure, for example $\Delta p$, $p_{pp}$, is to be determined and is to be regulated to a constant value or a desired value range. The regulation preferably takes place by setting the blood pump rate or the blood speed $Q_b$.

The above-named relationship forms the starting basis:

$$I_M = a + b \cdot Q_b + c \cdot Q_b \cdot \Delta P.$$

The total differential of this equation produces $dI_M = b \cdot dQ_b + c \cdot dQ_b \cdot \Delta p + c \cdot Q_b \cdot d\Delta p$. The partial derivation at a constant pressure $\Delta p$ produces:

$$(\partial I_M / \partial Q_b)_{\Delta p} = b + c \cdot \Delta p = \text{const}.$$

After the partial derivation at a constant pressure $\Delta p$, there results for $\Delta p = \text{const}$ on a comparison with equation (1):

$$(I_M - a)/Q_b = b + c \cdot \Delta p = \text{const}.$$

The sensitivity $E_{\Delta p}$ of the motor current with respect to the pressure change of $\Delta p$ is obtained from the partial derivation at a constant blood flow $Q_b$:

$$E_{\Delta p} = \Delta I_M / \Delta(\Delta p) = (\partial I_M / \partial \Delta p)_{Q_b} = c \cdot Q_b$$

A possible procedure for operating the system or for regulating the pressure comprises the measured values $I_M$ and $Q_b$ being noted or stored at regular intervals as start values $I_{M,0}$ and $Q_{b,0}$ in the non-faulty state, that is in the normal operation of the pumps and in particular also of the substituate pump.

If a fault occurs during the treatment, a check can first be made whether a maximum permitted pressure change has been reached. This maximum pressure change can be represented by $\Delta(\Delta p)_{GW}$. The change of the motor current is monitored for this purpose. It is conceivable that if the motor current changes by more than $$\Delta I_M = c \cdot Q_b \cdot \Delta(\Delta p)_{GW},$$

the active regulation phase is started in which regulation takes place to a pressure value or to a pressure value range.

When taking account of the recorded or noted start values for the motor current and the blood flow, the blood flow can now be changed by the regulation or by a regulating unit such that the relationship $(I_M(t)-a)/Q_b(t) = (I_{M,0}-a)/Q_{b,0}$ =const remains constant.

It is furthermore conceivable that the procedure is ended after a timeout or after a certain conveyed blood volume. The blood flow is then set back to the original value $Q_{b,0}$.

As can be seen from the above-named relationship for the keeping constant of the pressure, the parameter b is not needed and the parameter c is only needed at a trigger point in time, namely when it is to be determined whether the permitted pressure change has been exceeded or not. This value c does not have to be very precise. The accuracy of the parameter a only plays a role with relatively large changes.

Only one system parameter, namely a, has to be determined from the initially named parameters a, b and c. It is sufficient to measure the motor current $I_M$ at a low flow e.g. $Q_b$<100 ml/minute and at a low pressure $\Delta p$, for example within the framework of the preparation or on the filling of the hose system.

FIG. 3 shows an example for a current supply with a shunt resistance. In this case, a shunt resistance $R_{Shunt}$=0.1Ω is inserted into the 24 volt supply line of the motor. The voltage drop at the shunt is converted by a high-side current filler into an output current or output voltage with a ground (GND) reference and is digitized via an ADC. The further signal processing takes place in an microcontroller.

This results from the representation in accordance with FIG. 4.

The fit parameters a, b, and c can be determined as follows: The fit parameters are selected so that the sum of the error square S becomes minimal. The sum of the error square is $S = \Sigma(I_{M,i} - a - b \cdot Q_{b,i} - c \cdot Q_{b,i} \cdot \Delta p_i)^2$, where the sum is respectively formed over i in this relationship and in the following equations.

The extreme value of S is determined for this purpose:

$$\partial S / \partial a = 0 \rightarrow \Sigma(I_{M,i} - a - b \cdot Q_{b,i} - c \cdot Q_{b,i} \cdot \Delta p_i) = 0$$

$$\rightarrow \Sigma I_{M,i} = N \cdot a + b \cdot \Sigma Q_{b,i} + c \cdot \Sigma(Q_{b,i} \cdot \Delta p_i)$$

$$\rightarrow y_1 = a \cdot s_{1,1} + b \cdot s_{2,1} + c \cdot s_{3,1}$$

$$\partial S / \partial b = 0 \rightarrow \Sigma(I_{M,i} - a - b \cdot Q_{b,i} - c \cdot Q_{b,i} \cdot \Delta p_i) \cdot Q_{b,i} = 0$$

$$\rightarrow \Sigma I_{M,i} \cdot Q_{b,i} = a \cdot \Sigma Q_{b,i} + b \cdot \Sigma Q_{b,i}^2 + c \cdot \Sigma(Q_{b,i}^2 \cdot \Delta p_i)$$

$$\rightarrow y_2 = a \cdot s_{1,2} + b \cdot s_{2,2} + c \cdot s_{3,2}$$

$$\partial S / \partial c = 0 \rightarrow \Sigma(I_{M,i} - a - b \cdot Q_{b,i} - c \cdot Q_{b,i} \cdot p_i) \cdot Q_{b,i} \cdot \Delta p_i = 0$$

$$\rightarrow \Sigma(I_{M,i} \cdot Q_{b,i} \cdot \Delta p_i) = a \cdot \Sigma(Q_{b,i} \cdot \Delta p_i) + b \cdot \Sigma(Q_{b,i}^2 \cdot \Delta p_i) + c \cdot \Sigma(Q_{b,i} \cdot \Delta p_i)^2$$

$$\rightarrow y_3 = a \cdot s_{1,3} + b \cdot s_{2,3} + c \cdot s_{3,3}$$

The three equations for determining $y_1$, $y_2$ and $y_3$ can be combined to one vector equation: $y = a \cdot s_1 + b \cdot s_2 + c \cdot s_3$ With the aid of the determinant det( ), the solutions are obtained:

$a = \det(y; s_2; s_3)/\det(s_1; s_2; s_3)$
$b = \det(s_1; y; s_3)/\det(s_1; s_2; s_3)$
$c = \det(s_1; s_2; y)/\det(s_1; s_2; s_3)$

The invention claimed is:

1. A method for regulating or controlling the pressure (p) or a parameter correlated with the pressure (p) in an extracorporeal blood circuit of a blood treatment device, wherein the pump driven by the motor (M) is located in the blood circuit, the method comprising
   determining the pressure (p) or a parameter correlated therewith by a method comprising
     measuring the motor current ($I_M$) of the motor (M) and the blood flow ($Q_b$) or a parameter correlated therewith, wherein the pressure (p) or the parameter correlated therewith is calculated from the measured values, and
   determining the pressure difference ($\Delta p$) between upstream and downstream of the pump in accordance with the formula $I_M = a + b*Q_b + c*Q_b*\Delta_p$, wherein
     $a = P_0/U_0$, with $P_0$ being constant power consumption of the motor (M) and $U_0$ being voltage output by voltage supply for the motor (M),
     $b = (\mu \cdot F_N)/U_0 \cdot (2\pi \cdot R)/V_S$, with $(\mu \cdot F_N)$ being the power losses of the pump, R being radius of the blood pump motor (M), and $V_S$ being stroke volume of the blood pump per revolution, and
     $c = 1/U_0$, and
   changing the blood flow ($Q_b$) conveyed by the blood pump for the purpose of regulating or controlling.

2. A method in accordance with claim 1, characterized in that the method comprises the restriction of the pressure (p) or of a parameter correlated with, the pressure (p) such that a limit value is not exceeded.

3. A method in accordance with claim 1, characterized in that the method comprises the regulation of the pressure (p) or of a parameter correlated with the pressure (p) to a desired value or to a desired value range.

4. A method in accordance with claim 3, characterized in that a maximum permitted change of the pressure (p) or of a parameter correlated with the pressure (p) is predefined; and in that the regulation is only carried out when this maximum permitted change is reached or exceeded.

5. A method in accordance with claim 1, characterized in that the regulation is carried out such that the relationship $(I_M(t)-a)/Q_b(t) = (I_{M,0}-a)/Q_{b,0}$ remains constant, where t is time, $I_{M,0}$ and $Q_{b,0}$ are start values of the motor current ($I_M$) and of the blood flow ($Q_b$) at a point in time before a fault occurs, by restricting the pressure (p) or of a parameter correlated with the pressure (p) such that a limit value is not exceeded.

6. A blood treatment apparatus comprising at least one extracorporeal blood circuit containing at least one blood pump driven by at least one motor (M), at least one means for measuring the motor current ($I_M$), at least one means for measuring the blood flow ($Q_b$) or parameter correlated therewith, at least one of a calculating unit, control unit, and regulation unit configured to carry out a method on the basis of the measured values provided by the means, the method comprising measuring the motor current ($I_M$) of the motor (M) and the blood flow ($Q_b$) or a parameter correlated therewith, wherein the pressure (p) or the parameter correlated therewith is calculated from the measured values, and determining the pressure difference ($\Delta p$) between upstream and downstream of the pump in accordance with the formula $I_M = a + b*Q_b + c*Q_b*\Delta_p$, wherein $a = P_0/U_0$, with $P_0$ being constant power consumption of the motor (M) and $U_0$ being voltage output by voltage supply for the motor (M), $b = (\mu \cdot F_N)/U_0 \cdot (2\pi \cdot R)/V_S$, with ($\mu \cdot F_N$) being the power losses of the pump, R being radius of the blood pump motor (M), and $V_S$ being stroke volume of the blood pump per revolution, and $c = 1/U_0$.

7. A blood treatment apparatus in accordance with claim 6, characterized in that at least one of the blood pump is a peristaltic pump and the motor (M) is a DC motor operated with DC current.

8. A blood treatment apparatus in accordance with claim 6 further comprising at least one dialyzer having at least one chamber flowed through by blood in operation provided in the extracorporeal circuit.

9. A blood treatment apparatus in accordance with claim 8, characterized in that the dialyzer has at least one chamber flowed through by dialysis fluid in operation.

10. A blood treatment apparatus in accordance with claim 6 further comprising at least one substitute pump for supplying a substitution fluid to the blood in the extracorporeal circuit via at least one of a line upstream of the dialyzer and a line downstream of the dialyzer.

11. A blood treatment apparatus in accordance with claim 6 further comprising no pressure sensor except a venous pressure sensor provided downstream of the blood pump.

* * * * *